United States Patent [19]

Elnagar et al.

[11] Patent Number: 5,103,035
[45] Date of Patent: Apr. 7, 1992

[54] PROCESS FOR PREPARING BIS(ALKYLPHENYL)PENTAERYTHRITOL DIPHOSPHITES

[75] Inventors: Hassan Y. Elnagar; Kestutis A. Keblys, both of Baton Rouge, La.

[73] Assignee: Ethyl Corporation, Richmond, Va.

[21] Appl. No.: 505,166

[22] Filed: Apr. 5, 1990

[51] Int. Cl.⁵ ............................................. C07F 9/6574
[52] U.S. Cl. ........................................ 558/96; 558/78
[58] Field of Search .................................... 558/78, 96

[56] References Cited

U.S. PATENT DOCUMENTS

| | | | |
|---|---|---|---|
| 3,192,243 | 6/1965 | Gagliani | 558/78 |
| 3,310,609 | 3/1967 | Baranauckas et al. | 558/78 |
| 3,697,463 | 10/1972 | Oakes et al. | 260/23 X |
| 4,305,866 | 12/1981 | York et al. | 260/45.7 PH |
| 4,312,818 | 1/1982 | Maul et al. | 558/95 |
| 4,665,211 | 5/1987 | Martin et al. | 558/78 |
| 4,692,539 | 8/1987 | Spivack | 558/78 |
| 4,692,540 | 9/1987 | Illy et al. | 558/78 |
| 4,739,090 | 4/1988 | Tajima et al. | 558/78 |

FOREIGN PATENT DOCUMENTS

| | | |
|---|---|---|
| 761954 | 6/1967 | Canada . |
| 0143464 | 6/1985 | European Pat. Off. . |
| 0159294 | 10/1985 | European Pat. Off. . |
| 0186628 | 7/1986 | European Pat. Off. . |
| 1511105 | 5/1978 | United Kingdom . |
| 2046273 | 11/1980 | United Kingdom . |

*Primary Examiner*—Mary C. Lee
*Assistant Examiner*—Michael G. Ambrose
*Attorney, Agent, or Firm*—Edgar E. Spielman, Jr.; Patricia J. Hogan

[57] ABSTRACT

Bis(alkylphenyl)pentaerythritol diphosphite is produced by forming a reaction mass from phosphorous trichloride, pentaerythritol, a chlorinated hydrocarbon solvent and a heterocyclic tertiary amine catalyst followed by the addition of an alkylphenol to the reaction mass. The process further features the use of mild conditions.

10 Claims, No Drawings

PROCESS FOR PREPARING BIS(ALKYLPHENYL)PENTAERYTHRITOL DIPHOSPHITES

BACKGROUND OF THE INVENTION

This invention relates to a process for preparing cyclic phosphites which are useful as stabilizers for polymer compositions.

One of the most commercially significant cyclic phosphites is bis(alkylphenyl)pentaerythritol diphosphite. This diphosphite can have either of the following structures,

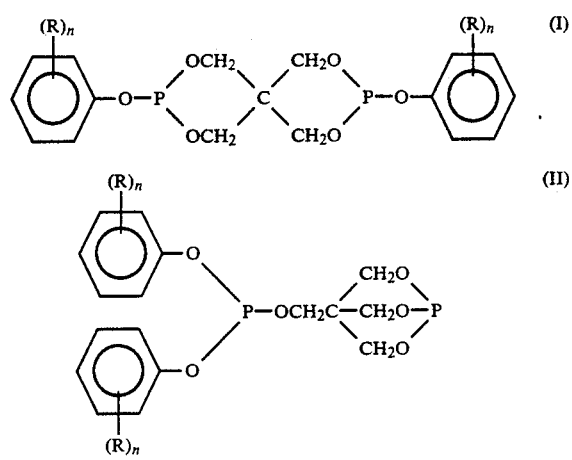

wherein each R is an independently selected alkyl group containing 3 to 12 carbon atoms. Both of these structures are contemporaneously produced by most bis(alkylphenyl)pentaerythritol diphosphite processes.

The structure (I) diphosphite is preferred while the structure (II) diphosphite is considered an impurity. It is preferred that no more than about 3 weight percent of the structure (II) diphosphite be present in a commercial product.

Many processes have been proposed for producing bis(alkylphenyl)pentaerythritol) diphosphite. See, for example, the several processes described in U.S. Pat. No(s). 4,305,866 and 4,665,211. Also see European Patent Application Nos. 0 143 464, 0 159 294, and 0 186 628, and United Kingdom patent No. 2046273B.

Most, if not all, of the processes feature long reaction times, severe reaction conditions, expensive reagents, low yields and/or a low product purity.

The Invention

Bis(alkylphenyl)pentaerythritol diphosphites are produced with good reaction efficiency and economy when produced in accordance with the process of this invention.

The process comprises, (a) forming a reaction mass by adding phosphorous trichloride to a reaction vessel previously charged with pentaerythritol, a chlorinated hydrocarbon solvent and a heterocyclic tertiary amine catalyst, and (b) adding, to the reaction mass, alkylphenol in an amount sufficient to yield a bis(alkylphenyl)pentaerythritol diphosphite product.

The amount of phosphorous trichloride and pentaerythritol used in forming the reaction mass is that amount which provides a molar ratio of from about 1.9 to about 2.3 moles of phosphorous trichloride per mole for pentaerythritol. Preferably, the molar ratio is substantially a two to one ratio. Use of less than two moles of phosphorous trichloride per mole of pentaerythritol can result in a reduction in the process yield, while more than two moles of phosphorous trichloride per mole of pentaerythritol can result in the production of undesirable phosphorus by-products which may require additional process step(s) for their removal. If process yield and the presence of phosphorous impurities in the reaction mass are of no concern to the practitioner, then the molar ratio can be adjusted to suit whatever other needs which are deemed to be important.

The chlorinated hydrocarbon solvent is inert in the process and is present in an amount sufficient to maintain the stirrability of the reactor contents during the process. Generally, from about 3 L to about 10 L of solvent per kilogram of pentaerythritol charged to the reaction vessel are suitable. Most preferably, from about 4 L to about 8 L per kilogram are used. All of the solvent is preferably charged to the reaction vessel at the beginning of the process. However, such is not necessary and may not even be preferred in certain circumstances. For example, a portion of the solvent can be added initially, with the remainder being added during the process as needed.

The chlorinated hydrocarbon solvent preferably is one containing 1 to 4 carbon atoms. Particularly preferred solvents are methylene chloride, 1,2-dichloroethane, trichloroethylne, perchloroethylene, chloroform, carbon tetrachloride and mixtures of any two or more of the foregoing. A most highly preferred solvent is methylene chloride.

The heterocyclic tertiary amine catalyst is used in an amount which is within the range of from about 0.005 to about 0.1 mole of catalyst per mole of pentaerythritol charged. Preferred amounts are within the range of from about 0.01 to about 0.02 mole of catalyst per mole of pentaerythritol.

The heterocyclic tertiary catalyst is preferably pyridine, quinoline or the alkylated derivatives thereof. The catalyst can also be comprised of a mixture of two or more of the foregoing. The alkyl substituents are exemplified by methyl, ethyl, isopropyl, tert-butyl, butyl, etc. groups. Examples of the mixtures are: 2-methyl pyridine and 4-methyl pyridine; 2-methyl-4-ethyl pyridine and quinoline; and 3-ethyl quinoline and 3,5-dimethyl pyridine; and N,N-dimethylamino-pyridine could also be used. The preferred catalysts are pyridine and its alkylated derivatives. Most preferred is pyridine.

The phosphorus trichloride is a liquid under the process conditions and, as such, can be added to the reaction vessel at a rate which is convenient in view of the evolution of HCl from the reaction mass.

During the phosphorus trichloride addition, the reaction vessel contents are kept under mild conditions, i.e., a temperature within the range of from about 30° C. to about 50° C. and a pressure of atmospheric. While temperatures much in excess of 40° C. can be used, they are not generally needed. Temperatures lower than about 30° C. are not the temperatures of choice as the reaction time is unnecessarily increased. Preferred temperatures are within the range of from about 35° C. to about 40° C. For ease in controlling the temperature, it is preferred that the reaction mass be kept in a refluxing condition. The refluxing condition may require superatmospheric pressure depending on the particular temperature chosen.

After at least substantial completion of the phosphorous trichloride addition step, alkylphenol can be added to the reaction mass. It is preferred that the alkylphenol be added after the phosphorous trichloride-pentaerythritol reaction has slowed or stopped. This should occur within from about 0.5 to about 2.0 hours after the phosphorous trichloride addition is complete.

The amount of alkylphenol added preferably provides two moles of alkylphenol for every mole of pentaerythritol charged to the reaction vessel. Small deviations from this approximate 2:1 molar ratio are acceptable, however, large deviations, say 10 percent to 20 percent, can result in the presence of impurities in the final product, e.g., reaction intermediates, unreacted alkylphenol, etc. A preferred working ratio is from about 2.0:1 to about 2.2:1.

The alkylphenol can be added as a solid or as a solute portion of a solution. The addition rate for the alkylphenol is not critical. It is preferred to add the phenol in its simplest form, i.e., as a solid. If the alkylphenol is added as a solution, the solvent should be inert to the process. Suitable solvents are methylene chloride, toluene and the like. On a laboratory scale, the rate of addition can include substantially instantaneous addition. For larger scale processes, the upper end of the rate of addition is dependent upon the ability of the process equipment to thoroughly mix in the alkylphenol and the avoidance of lumping and/or bridging problems. As a general guideline, the time of addition, for most all process scales, will fall within the range of from about 15 minutes to about two hours.

The alkylphenol can be a mono-, di- or tri- alkyl substituted phenol. The alkyl substituent can contain from 1 to 12 carbon atoms. Exemplary alkyl substituents are methyl, ethyl, propyl, sec-butyl, tert-butyl, pentyl, 2,2-methyl propyl, isooctyl, tert-octyl, nonyl, cyclopentyl, cyclohexyl, phenylmethyl, 1-phenylethyl, etc. Preferred alkylphenols are 2,4-di-tert-butylphenol and 2,6-di-tert-butyl-4-methylphenol.

During and after the alkylphenol addition, the reaction vessel contents are maintained at a temperature within the range of from about 40° C. to about 50° C. and preferably within the range of from about 45° C. to about 48° C. The pressure is preferably about atmospheric. It is most preferred to keep the reaction vessel contents at a refluxing condition. It may be necessary to use sub-atmospheric or super-atmospheric pressure to achieve the refluxing condition depending on the temperature chosen.

After the alkylphenol has been added, the resultant reaction mass is kept at the above described temperature and pressure for a ride time sufficient to insure production of the desired bis(alkylphenyl)pentaerythritol diphosphite. To obtain good yields, say greater than 95 percent, the ride time will be within the range of from about 5 to about 12 hours, and preferably within the range of from about 9 to about 11 hours. Since HCl is evolved during the reaction, monitoring of the HCl evolution for its cessation is a convenient way to select the ride time needed for each particularly designed process to obtain its maximum yield of bis(alkylphenyl)pentaerythritol diphosphite.

Subsequent to the ride time, the recovery of the desired bis(alkylphenyl)pentaerythritol diphosphite can be effected. A preferred recovery sequence, which gives a very pure produce, includes: (a) cooling the reaction mass to room temperature; (b) neutralizing in the reaction mass, for example, by bubbling ammonia gas therethrough; (c) removing the solid neutralization salt, e.g. $NH_4Cl$, from the reaction mass via a liquid-solid separation technique; (d) adding an alcohol, e.g., isopropanol; (e) distilling off the chlorinated hydrocarbon solvent; and (f) after cooling, separating the solid bis(alkylphenyl)pentaerythritol diphosphite from the remaining alcohol. The alcohol used is preferably isopropanol. Other alcohols can be used provided that their boiling point is higher than that of the chlorinated hydrocarbon solvent and provided that the bis(alkylphenyl)pentaerythritol diphosphite product is essentially insoluble therein. The amount of alcohol used can be within the range of from about 0.5 L to about 1.5 L per liter of methylene chloride solvent used in the process.

Other techniques can be used to effect recovery of the bis(alkylphenyl)pentaerythritol diphosphite product. For example, the foregoing recovery sequence, minus steps (a), (b) and (c), can be used if acid contamination is not a concern. Even further, since the diphosphite product is soluble in the methylene chloride, it is possible to effect its recovery by simply evaporating away all the methylene chloride. This is not a preferred technique as it does not provide for the removal of potential impurities.

To insure that the reaction vessel contents are well mixed during the process of this invention, it is advisable to provide for a mixing mechanism, e.g. a reaction vessel stirrer.

To achieve and maintain the reaction vessel contents at the chosen temperatures, it will generally be necessary to provide a heat source, e.g. a flask heating mantle, or a steam traced reaction vessel.

The principal reactions which are believed to occur during the process of this invention are represented by the following:

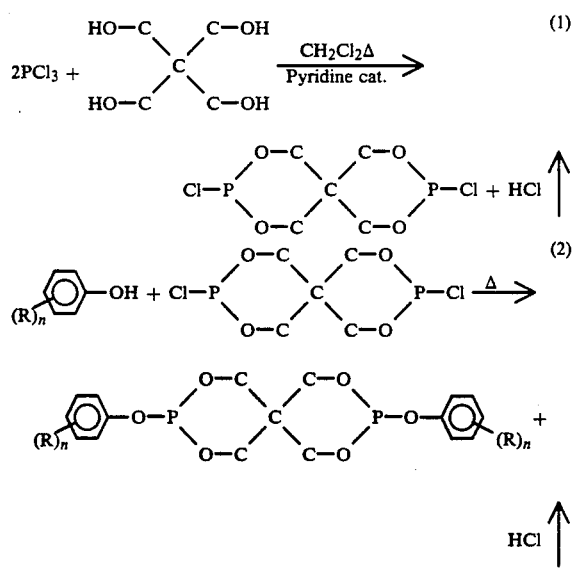

EXAMPLE I

To a 1000 mL stirred flask fitted with a condenser, trap and caustic scrubber was added pentaerythritol (68 g) and pyridine (3 mL) in $CH_2Cl_2$ (300 mL). $PCl_3$ (87 mL) was then carefully added over a period of 10 minutes. Hydrogen chloride (HCl) started to evolve after the addition was completed. Evolved HCl was trapped overhead and neutralized in the caustic scrubber. The reaction mixture was heated to 38°–40° C. The solution became completely clear after 90 minutes. Solid 2,4-di-tert-butylphenol (220 g) was added in about 20 minutes and HCl started to evolve again. Heating continued for 8 hours. After this period, the mixture was sampled and NMR showed essentially complete conversion to bis(2,4-di-tert-butylphenyl)pentaerythritol diphosphite. Additional $CH_2Cl_2$ (300 mL) was added to dissolve the product while heating. After the dissolution was achieved, the solution was cooled and ammonia gas was bubbled therethrough. The precipitate was removed by filtration, and the filtrate was poured into 400 mL isopropyl alcohol. The resultant mix was heated to 40°–55° C. to distill off the $CH_2Cl_2$. The resulting alcohol-crystal slurry was cooled to room temperature and then was filtered to recover the solid therefrom. The recovered solids were dried under reduced pressure to obtain a total of 215 g of pure product (73 percent yield). This product was analyzed by phosphorus NMR and shown to be bis(2,4-di-t-butylphenyl)pentaerythritol diphosphite, structure (I). The purity was greater than 99.99 percent.

As can be seen by the above results, the process of this invention produces a highly pure product in good yields despite the fact that relatively mild reaction conditions are used and the reaction time is not of undue length. Also, the process does not produce a product with any significant amount of bis(alkylphenyl)pentaerythritol diphosphite which has the "caged" type (II) structure. Even further, the process of this invention utilizes a simple, single pot, two-step procedure and does not require recovery of an intermediate or removal of $PCl_3$ from the reaction mass. In addition to the foregoing, the recovery scheme illustrated in Example I yields pure product with only marginal affect on overall process yield.

EXAMPLE II

The apparatus that was used in Example I was used again. To a slurry in the flask that was comprised of pentaerythritol (34 g), pyridine (1.5 mL) and methylene chloride (200 mL) was added $PCl_3$ (45 mL) over a period of 10 minutes. The mixture was heated at 40° C. and became clear after 50 minutes. Heating continued for an additional 55 minutes and solid 2,4-di-tert-butylphenol (110 g) was added over a 5 minute period. The mixture was stirred for 17 hours at 46° C., then, after diluting the reaction mixture with $CH_2Cl_2$ (200 mL) ammonia gas was bubbled through to neutralize the excess HCl and an ammonium chloride precipitate was formed. The solid ammonium chloride was filtered off and the filtrate was added to isopropyl alcohol (300 mL). The methylene chloride was collected by distillation. The remaining isopropanol slurry was cooled to room temperature, the solids were filtered therefrom and dried under reduced pressure to afford a total of 95.2 g product. Phosphorus NMR revealed exceptional product purity for structure (I) diphosphites. Structure (II) diphosphites were not detected.

Exemplary bis(alkylphenyl)pentaerythritol diphosphites which can be produced by the processes of this invention are bis(2,4-di-tert-butylphenyl)pentaerythritol diphosphite, bis-(2-tert-butyl-4-methylphenyl)pentaerythritol diphosphite, bis(2,4-dihexylphenyl)pentaerythritol diphosphite, bis(2,6-di-tert-butylphenyl)pentaerythritol diphosphite, bis(2,6-di-tert-butyl-4-methylphenyl)pentaerythritol diphosphite.

What is claimed is:

1. A process which comprises:
   (a) adding 1.9–2.3 molar proportions of phosphorous trichloride to a solution in a chlorinated hydrocarbon solvent of one molar proportion of pentaerythritol and 0.005–0.1 molar proportion of a heterocyclic tertiary amine catalyst selected from pyridine, alkylpyridines, quinoline, alkylquinolines, and mixtures thereof,
   (b) heating the resultant mixture at about 30°–50° C. to react the phosphorous trichloride and pentaerythritol,
   (c) adjusting the temperature, if necessary, to be in the range of about 40°–50° C.,
   (d) adding about 2.0–2.2 molar proportions of an alkylphenol, and
   (e) reacting the alkylphenol with the phosphorous trichloride/pentaerythitol reaction product at about 40°–50° C. to form a bis(alkylphenyl)pentaerythritol diphosphite.

2. The process of claim 1 wherein the alkylphenol is 2,4-di-t-butylphenol.

3. The process of claim 1 wherein the catalyst is pyridine, an alkylpyridine, or a mixture thereof.

4. The process of claim 3 wherein the catalyst is pyridine.

5. The process of claim 1 wherein the solvent is a chlorinated hydrocarbon containing 1–4 carbons.

6. The process of claim 5 wherein the solvent is methylene chloride.

7. The process of claim 1 wherein the phosphorous trichloride/pentaerythritol and alkylphenol/pentaerythritol mol ratios are about 2/1.

8. The process of claim 1 wherein addition of the alkylphenol is begun about 0.5–5 hours after completion of the phosphorous trichloride feed, and the reaction temperature is maintained for about 5–20 hours after completion of the alkylphenol feed.

9. The process of claim 1 conducted at reflux temperature.

10. A process which comprises:
    (a) adding about two molar proportions of phosphorous trichloride to a solution in methylene chloride of one molar proportion of pentaerythritol and 0.005–0.1 molar proportion of pyridine,
    (b) refluxing the resultant mixture for 0.5–5 hours to react the phosphorous trichloride and pentaerythritol,
    (c) adding about two molar proportions of 2,4-di-t-butylphenol, and
    (d) continuing to reflux the reaction mixture for about 5–20 hours to react the 2,4-di-t-butylphenol with the phosphorous trichloride/pentaerythritol reaction product to form bis(2,4-di-t-butylphenyl)pentaerythritol diphosphite.

* * * * *